United States Patent
Magnusson et al.

(10) Patent No.: US 11,413,190 B2
(45) Date of Patent: Aug. 16, 2022

(54) PROTECTIVE HEADGEAR COMPRISING A CURVED SWITCHABLE SHUTTER AND COMPRISING MULTIPLE ANTIREFLECTIVE LAYERS

(71) Applicant: 3M INNOVATIVE PROPERTIES COMPANY, St. Paul, MN (US)

(72) Inventors: Kristina M. Magnusson, Djurmo (SE); Kenneth Jarefors, Borlänge (SE); Britton G. Billingsley, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 273 days.

(21) Appl. No.: 16/938,372

(22) Filed: Jul. 24, 2020

(65) Prior Publication Data

US 2020/0390606 A1 Dec. 17, 2020

Related U.S. Application Data

(63) Continuation of application No. 16/096,939, filed as application No. PCT/US2017/031545 on May 8, 2017, now Pat. No. 10,758,420.

(60) Provisional application No. 62/335,256, filed on May 12, 2016.

(51) Int. Cl.
| | |
|---|---|
| *G02B 5/28* | (2006.01) |
| *A61F 9/06* | (2006.01) |
| *G02B 5/20* | (2006.01) |
| *G02B 1/11* | (2015.01) |
| *A61F 9/04* | (2006.01) |

(52) U.S. Cl.
CPC ............ *A61F 9/062* (2013.01); *A61F 9/04* (2013.01); *A61F 9/061* (2013.01); *A61F 9/067* (2013.01); *G02B 1/11* (2013.01); *G02B 5/20* (2013.01)

(58) Field of Classification Search
CPC ... G02B 1/00; G02B 1/10; G02B 1/11; G02B 1/115; G02B 5/00; G02B 5/003; G02B 5/20; G02B 5/205; G02B 5/208; G02B 5/22; G02B 5/23; G02B 5/28; G02B 5/281; G02B 5/282; G02B 5/283; A61F 9/02; A61F 9/022; A61F 9/023; A61F 9/04; A61F 9/06; A61F 9/061; A61F 9/062; A61F 9/067
USPC .............. 359/577–590, 601–614, 885–892
See application file for complete search history.

(56) References Cited

U.S. PATENT DOCUMENTS

| | | |
|---|---|---|
| 2,758,510 A | 8/1956 | Auwarter |
| 3,235,397 A | 2/1966 | Millendorfer |
| 3,432,225 A | 3/1969 | Rock |
| 3,781,090 A | 12/1973 | Sumita |
| 3,936,579 A | 2/1976 | Ogasawara |

(Continued)

FOREIGN PATENT DOCUMENTS

| | | |
|---|---|---|
| CN | 101825732 A | 9/2010 |
| CN | 104955350 A | 9/2015 |

(Continued)

OTHER PUBLICATIONS

International Search Report for PCT International Application No. PCT/US2017/031545, dated Aug. 18, 2017, 3 pages.

*Primary Examiner* — Thong Q Nguyen
(74) *Attorney, Agent, or Firm* — Kenneth B. Wood

(57) ABSTRACT

Protective headgear with a curved switchable shutter and curved front and rear cover plates and including at least two antireflective layers.

17 Claims, 6 Drawing Sheets

(56) References Cited

U.S. PATENT DOCUMENTS

| | | |
|---|---|---|
| 4,045,125 A | 8/1977 | Farges |
| 4,070,097 A | 1/1978 | Gelber |
| 4,169,655 A | 10/1979 | Jacobsson |
| 4,201,450 A | 5/1980 | Trapani |
| 5,150,238 A | 9/1992 | Vogeley |
| 5,198,267 A | 3/1993 | Aharoni |
| 5,579,162 A | 11/1996 | Bjornard |
| 5,579,163 A | 11/1996 | Peterson |
| 5,694,240 A | 12/1997 | Sternbergh |
| 5,729,323 A | 3/1998 | Arden |
| 5,825,441 A | 10/1998 | Hörnell |
| 5,846,650 A | 12/1998 | Ko |
| 6,074,730 A | 6/2000 | Laird |
| 6,097,451 A | 8/2000 | Palmer |
| 6,261,696 B1 | 7/2001 | Biro |
| 6,337,771 B1 | 1/2002 | Chu |
| 6,793,339 B1 | 9/2004 | Yip |
| 6,934,967 B2 | 8/2005 | Migashita |
| 7,477,330 B2 | 1/2009 | Magnusson |
| 7,717,557 B2 | 5/2010 | Kobayashi |
| 7,865,968 B2 | 1/2011 | Lilenthal |
| 7,884,888 B2 | 2/2011 | Magnusson |
| 8,042,958 B2 | 10/2011 | Sundell |
| 8,505,121 B2 | 8/2013 | Ahlgren |
| 9,038,198 B2 | 5/2015 | Feinberg |
| 9,291,745 B2 | 3/2016 | Nakashima |
| 9,581,733 B2 | 2/2017 | Tamada |
| 10,758,420 B2 * | 9/2020 | Magnusson ............. G02B 1/11 |
| 2009/0047504 A1 | 2/2009 | Wu |
| 2011/0119801 A1 | 5/2011 | Wright |
| 2011/0193814 A1 | 8/2011 | Gay |
| 2014/0013479 A1 | 1/2014 | Magnusson |
| 2014/0168546 A1 | 6/2014 | Magnusson |
| 2015/0033430 A1 | 2/2015 | Hofer Kraner |
| 2015/0077854 A1 | 3/2015 | Yu |
| 2016/0081856 A1 | 3/2016 | Hofer Kraner |
| 2018/0149895 A1 | 5/2018 | Hofer Kraner |

FOREIGN PATENT DOCUMENTS

| | | |
|---|---|---|
| EP | 0706674 | 4/1996 |
| JP | 60015318 U | 2/1985 |
| JP | 11514457 A | 12/1999 |
| KR | 100658036 B1 | 12/2006 |
| KR | 101239871 B1 | 3/2013 |
| WO | WO 1997/48002 | 12/1997 |
| WO | WO 2001-57579 | 8/2001 |
| WO | WO 2004-053586 | 6/2004 |
| WO | WO 2013-115970 | 8/2013 |
| WO | WO 2014-092989 | 6/2014 |
| WO | WO 2016-037544 | 3/2016 |
| WO | WO 2017-189394 | 11/2017 |
| WO | WO 2017-192421 | 11/2017 |

* cited by examiner

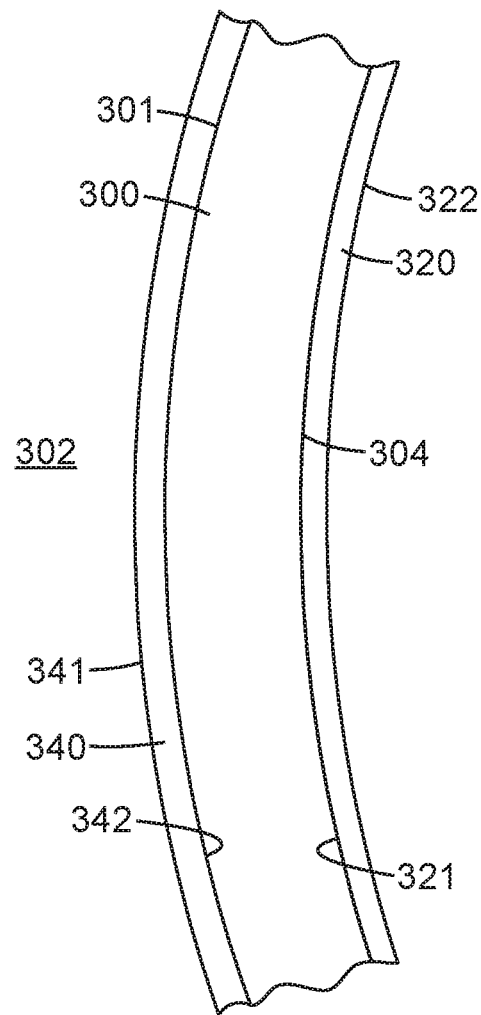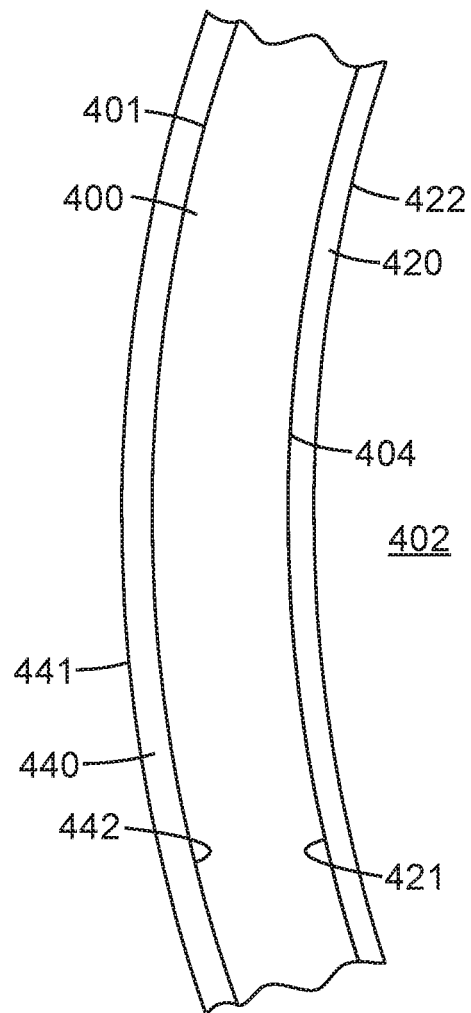
*Fig. 4*  *Fig. 5*

PROTECTIVE HEADGEAR COMPRISING A CURVED SWITCHABLE SHUTTER AND COMPRISING MULTIPLE ANTIREFLECTIVE LAYERS

BACKGROUND

Automatic darkening filters are often provided on protective headgear (e.g., helmets, shields, visors, or the like), e.g. where protection from high intensity light is desired.

GLOSSARY

The terms set forth below will have the meanings as defined:

"Automatic darkening filter" means a device that attenuates light (by way of a switchable shutter) in response to an input from the light itself and without an input from a person.

A "switchable shutter" is an electrically operated optical device that is capable of assuming at least a light state and a dark state.

"Curved" means not following a straight line when viewed in cross-section.

"Deformation" with respect to a glass layer means being able to be bent 5 millimeters (mm) over a cantilevered distance of 50 mm from the fixed point without fracture.

"Flexible" means being able to withstand deformation into a curved shape without breaking.

"Glass" means an inorganic amorphous non-crystalline solid material that is capable of transmitting visible light.

"Cover plate" refers to an optically transparent protective layer made of a suitably strong material, that serves to protect a switchable shutter of a headgear and/or to protect the eyes of a wearer of the headgear.

"Glass layer" or "glass sheet" means glass that has dimensions that are substantially greater in width and length than in thickness.

"Juxtaposed" means to place side by side (in overlapping relation) but not necessarily in contact with each other.

"Liquid crystal layer" means a layer that has molecules in a liquid phase which molecules have some orientational order with respect to each other and have the ability to align in response to an electric field.

"Low twist" means having a twist angle of less than 90 degrees.

"Optically-transparent" means that visible light can pass therethrough sufficiently to see the desired image on the opposing side of the structure.

An "optical component" refers to a component of a protective headgear through which light must pass to reach the wearer's eyes, and includes front and rear cover plates and a switchable shutter.

Terms such as "front", "frontward", "forward", and the like mean generally away from the face of a wearer of the protective headgear; terms such as "rear", "rearward", and the like mean generally toward the face of the wearer.

SUMMARY OF THE INVENTION

In broad summary, herein is disclosed a protective headgear comprising a curved switchable shutter and curved front and rear cover plates, and further comprising at least two antireflective layers. These and other aspects of the invention will be apparent from the detailed description below. In no event, however, should this broad summary be construed to limit the claimable subject matter, whether such subject matter is presented in claims in the application as initially filed or in claims that are amended or otherwise presented in prosecution.

BRIEF DESCRIPTION OF THE DRAWINGS

FIG. 4 is an isolated top view of an exemplary rear cover plate comprising an antireflective layer on a front side thereof and an antireflective layer on a rear side thereof.

FIG. 5 is an isolated top view of an exemplary front cover plate comprising an antireflective layer on a front side thereof and an antireflective layer on a rear side thereof.

Like reference numbers in the various figures indicate like elements. Some elements may be present in identical or equivalent multiples; in such cases only one or more representative elements may be designated by a reference number but it will be understood that such reference numbers apply to all such identical elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated. As used herein as a modifier to a property or attribute, the term "generally", unless otherwise specifically defined, means that the property or attribute would be readily recognizable by a person of ordinary skill but without requiring a high degree of approximation (e.g., within +/−20% for quantifiable properties). The term "substantially", unless otherwise specifically defined, means to a high degree of approximation (e.g., within +/−10% for quantifiable properties). The term "essentially" means to a very high degree of approximation (e.g., within plus or minus 2% for quantifiable properties; it will be understood that the phrase "at least essentially" subsumes the specific case of an "exact" match. However, even an "exact" match, or any other characterization using terms such as e.g. same, equal, identical, uniform, constant, and the like, will be understood to be within the usual tolerances or measuring error applicable to the particular circumstance rather than requiring absolute precision or a perfect match. All references herein to numerical parameters (dimensions, ratios, and so on) are understood to be calculable (unless otherwise noted) by the use of average values derived from a number of measurements of the parameter, particularly for the case of a parameter that is variable.

DETAILED DESCRIPTION

Figure 1:
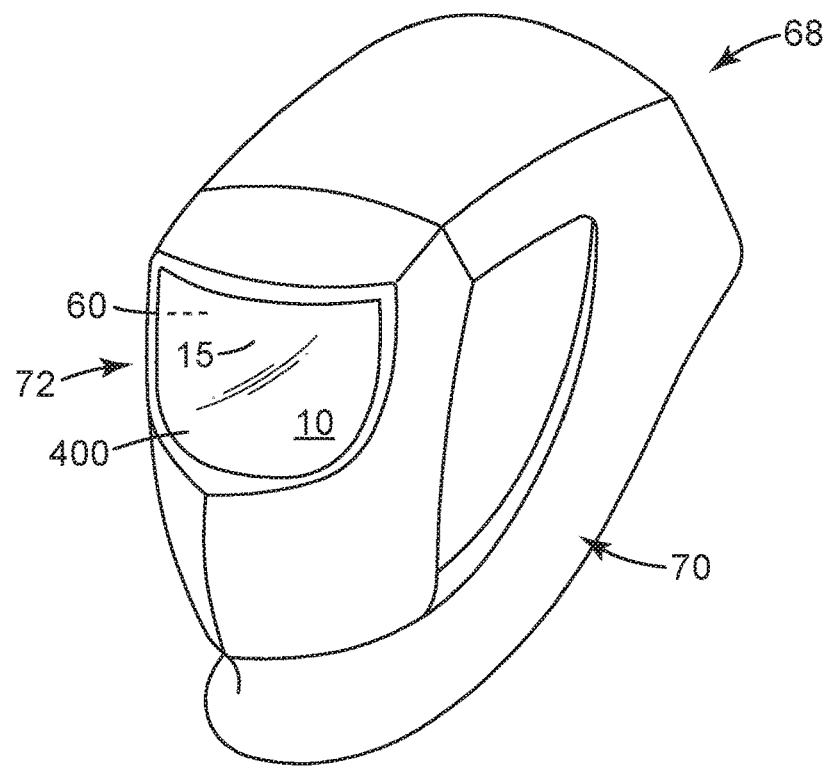
FIG. 1 is a front/side perspective view of an exemplary protective headgear comprising a curved autodarkening filter.

Shown in FIG. 1 in perspective view from the front side is an exemplary protective headgear 68 comprising an automatic darkening filter 60 and comprising at least two antireflective layers (not visible in FIG. 1). Protective headgear 68 comprises a main body 70 that contains an automatic-darkening filter 60 mounted within an at least generally front-facing opening (window) 72 of main body 70. Automatic-darkening filter 60 includes curved, switchable shutter 10 that is positioned so that any electromagnetic radiation (e.g., visible light, UV light, IR, etc.) that reaches the eyes of a person wearing the headgear must first pass through switchable shutter 10 to be optically filtered in any desired manner. Switchable shutter 10 may be positioned so that a laterally central area 15 of switchable shutter 10 is in front of the wearer's eyes when the headgear is worn by the user. As discussed in detail herein, switchable shutter 10 is at least somewhat curved. In some embodiments, shutter 10 may comprise areas (that will be integrally connected to, and extending from, central area 15) that wrap at least partially around the left and right lateral sides of the protective headgear to a desired extent. While a relatively small extent of side-wrap is present in the exemplary design of FIG. 1, any amount of side-wrap can be used as desired.

Switchable shutter 10 is configured to controllably block electromagnetic radiation; i.e., shutter 10 can be switched between at least a light state (e.g. in which is it relatively highly visible-light-transmissive) and a dark state (e.g. in which it is relatively non-transmissive to visible light). Such a switchable shutter may comprise e.g. one or more liquid crystal layers, polarizing filters, electrochromic materials, etc., as are familiar to those of ordinary skill. If desired, other components such as e.g. ultraviolet-blocking coatings, infrared-blocking coatings, interference filters, and the like, may be provided as part of shutter 10 (or, in general, as part of automatic darkening filter 60). Potentially suitable components and arrangements of automatic darkening filters and switchable shutters thereof are described later herein in detail, in various exemplary embodiments.

Figure 2:
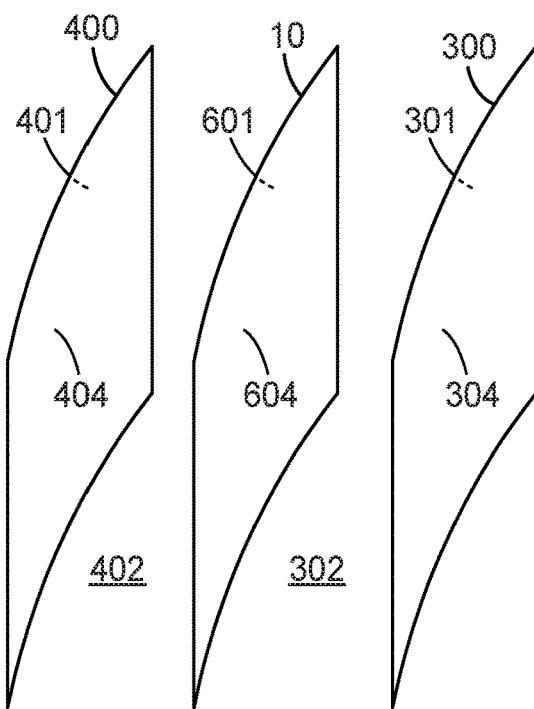
FIG. 2 is an exploded isolated perspective side view of an exemplary curved, switchable shutter and curved front and rear cover plates.
Figure 3:
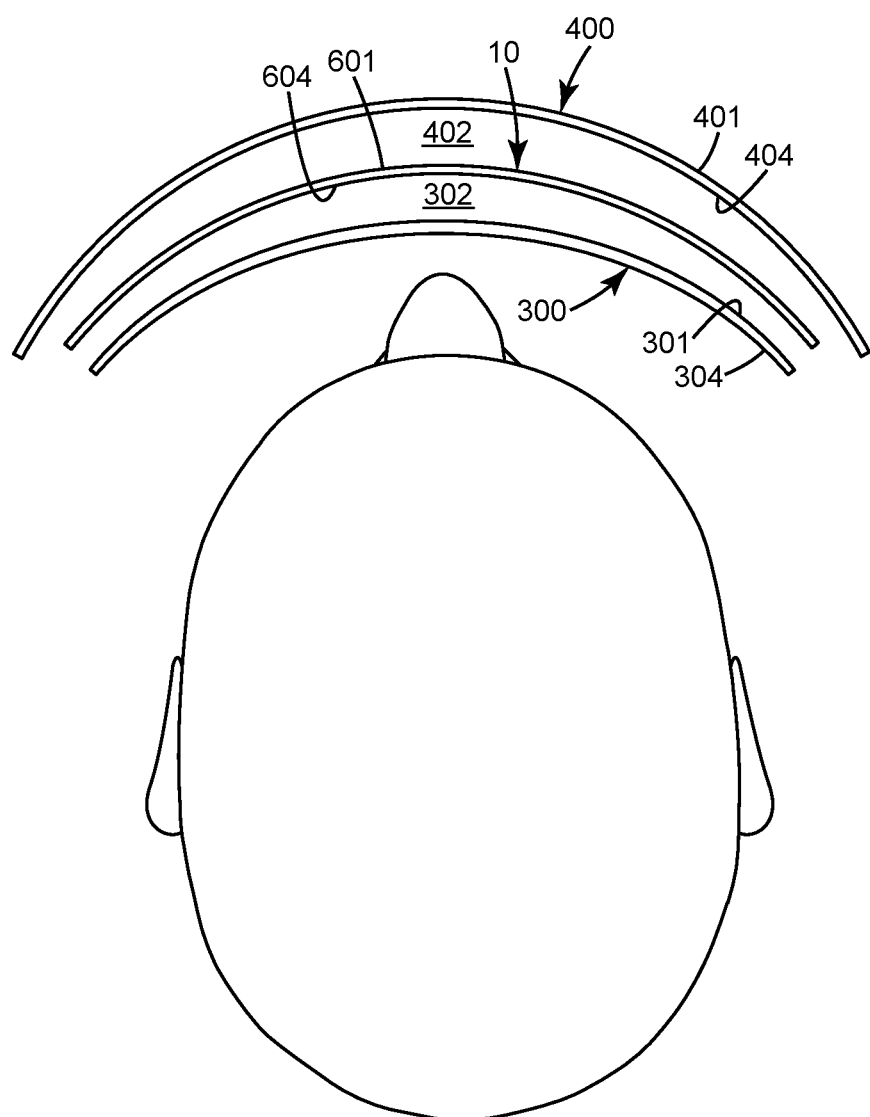
FIG. 3 is a top view of an exemplary curved, switchable shutter and curved front and rear cover plates, in relation to the head of a wearer of a protective headgear.

Protective headgear 68 comprises a front cover plate 400 and a rear cover plate 300, as shown in generic representation in the side view of FIG. 2 and as shown in relation to the head of a wearer of the protective headgear in the top view of FIG. 3. Cover plates 300 and 400 sandwich switchable shutter 10 therebetween and thus protect switchable shutter 10 e.g. from mechanical impacts, particulate debris, splashing liquids, and so on. (Such cover plates may also enhance the protection of the wearer of the headgear.) The term "plate" is used generically and does not require a cover plate to be planar. In fact, at least a portion of each cover plate will be curved. In some embodiments, each cover plate exhibits a curvature that at least generally matches with the curvature of the curved switchable shutter 10 (e.g. the front and rear cover plates and the curved switchable shutter may all three exhibit a convex front surface and a concave rear surface). This does not require that the curvatures must exactly match or that a surface of a cover plate must be exactly parallel to the surface of the shutter at any or all locations. For example, front cover plate 400 may be positioned on the front side of switchable shutter 10 so that, at all locations through which electromagnetic radiation may pass through these items, a distance (providing an air gap 402) of e.g. 0.5-4 mm is present between the rear surface 404 of the front cover plate 400 and the front surface 601 of switchable shutter 10. In some embodiments, this distance may be at least generally, substantially, or essentially constant over e.g. the lateral extent of the cover plate and shutter. In other embodiments the distance may vary (e.g., a front cover plate may bow outward in a frontward direction so that a larger air gap, e.g. of up to 10, 15 or even 20 mm, is present at laterally central portion 15 of shutter 10). Similar arrangements are possible for rear cover plate 300 relative to rear surface 604 of switchable shutter 10. In some embodiments, a front air gap 402 between the front cover plate and shutter 10, may be larger than a rear air gap 302 between the rear cover plate and the shutter (in view of the larger likelihood of the front cover plate being exposed to mechanical impacts and the like in use of the protective headgear).

A cover plate may be made of any material (e.g., an organic polymeric material, e.g. polycarbonate, polystyrene, polymethylmethacrylate, cyclic olefin copolymer, and the like) that possesses sufficient mechanical strength and integrity to protect switchable shutter 10, in combination with sufficient optical transparency. Particularly for a front cover plate, the plate material may be chosen to have enhanced resistance to elevated temperatures (as may occur e.g. in welding operations), to mechanical impacts, and so on. In particular embodiments, one or both cover plates 300 and 400 may be made of polycarbonate, which may be e.g. injection molded or obtained by suitably softening and bending a flat sheet. In some embodiments, front cover plate 400 and rear cover plate 300 may be of identical structure (size, shape and curvature) and composition in order to simplify tracking and production. In other embodiments, the front and rear cover plates may differ at least slightly in curvature (in such embodiments the cover plates may still be of the same composition if desired). In various embodiments a cover plate may exhibit a front-rear dimension (thickness) of from about 0.5, 1.0, 1.5, or 2.0 mm, to about 5.0, 4.0, 3.0, or 2.0 mm. A cover plate may take the form of a single layer of material; or, in some embodiments it may comprise multiple sublayers as long as this does not unacceptably affect the optical transparency of the cover plate.

In some embodiments, a cover plate may take the form of a curved slab of organic polymer material that exhibits a generally, substantially, or essentially uniform front-rear thickness throughout the entire area of the cover plate that is part of the optical path. In other embodiments, a cover plate (e.g., a rear cover plate) may exhibit a non-uniform front-rear thickness. In particular embodiments, such a cover plate may be thicker in areas that overlap laterally central area 15 of switchable shutter 10, and may be thinner in areas that are proximate the lateral edges of the cover plate. Such arrangements are discussed in detail in EP Patent Application No. 16 168 229.9, attorney docket number 78278EP002, filed 4 May 2016 and entitled "A curved eye protection shield for welding protection", which is incorporated by reference in its entirety herein. In some embodiments, a cover plate may comprise two optical lenses which in combination may only partially cover (i.e., overlap in the light path) curved switchable shutter 10. Such arrangements are discussed in detail in EP Patent Application No. 16 167 182.1, attorney docket number 77346EP002, filed 27 Apr. 2016 and entitled "Welding protector with magnifying cover", which is incorporated by reference in its entirety herein.

Cover plates 300 and 400 may be conveniently supplied separately from autodarkening filter 60 and switchable shutter 10 thereof, rather than being e.g. permanently attached to shutter 10. Cover plates 300 and 400 can be installed in headgear 68 (e.g., they can be mounted to window 72 and attached to a frame that surrounds the window) so as to sandwich shutter 10 therebetween. In some embodiments, cover plates 300 and/or 400 are removable from the headgear and can be cleaned and reinstalled or replaced as desired.

In some embodiments, the perimeter of a cover plate may be abutted directly against a frame of the protective headgear (e.g. of the main body of the headgear). In some embodiments, a resilient gasket may be provided against which the perimeter of the cover plate may rest. In variations of such an approach, a resilient gasket may be provided on the front side, the rear side, or on both sides, of the perimeter of switchable shutter 10. Such a gasket or gaskets may e.g. minimize the ability for dust to penetrate into air gaps 302 and/or 402; and/or, may enhance the ability to isolate switchable shutter 10 from impacts that are received by a cover plate and/or that are received by the main body of the protective headgear itself.

Front and rear covers 400 and 300 and switchable shutter 10 combine to define an optical path along which electromagnetic radiation has to travel to reach the eyes of a wearer of protective headgear 68. As noted above, cover plates can serve several useful purposes. However, in the present work it has been discovered that when a curved switchable shutter is used, the presence of cover plates (e.g. front and rear cover plates that are curved and that are positioned so that there is an air gap between each cover plate and the switchable shutter) in the optical path may have potentially disadvantageous effects.

A first potential effect results from the fact that light that enters the interior of the headgear along a path so as to not directly encounter the wearer's eyes, may nevertheless eventually encounter the wearer's eyes so as to cause undesirable optical phenomena. Such issues have been recognized to some extent in conventional protective headgear comprising planar shutters and/or cover plates (noting that the inner surfaces of welding helmets have often been made dark in color, and/or have comprised a matte finish, to minimize internal reflections). However, it has now been found that such problems can be particularly acute in the case of a curved shutter and cover plates. A first potential factor in this lies in the fact that a curved shutter may be configured to at least slightly wrap around the lateral sides of the headgear and thus may allow more light to enter the interior of the protective headgear without directly encountering the wearer's eyes. A second factor is that the curvature of the optical components (the front and rear cover plates and the shutter) of the headgear is such that any light that impinges upon them from the interior of the headgear and is reflected therefrom, will likely be directed toward the wearer's eyes, as is evident from inspection of FIG. 3. That is, a surface of one of the optical components may act somewhat like a parabolic reflector with the wearer's eyes being located near the focal point of the reflected light. This can result in, for example, the wearer being aware of reflected light (e.g. perceiving his or her own reflection), which may be undesirable. This potential problem is compounded (in comparison to the situation with regard to e.g. ordinary vision-protective glasses, safety glasses, sunglasses, and so on) by the fact that such reflections may occur at any or all of the numerous interfaces (in particular, interfaces between air and a solid substrate such as a cover plate or an outermost layer of a switchable shutter) that are present in the optical path of the protective headgear.

Another potentially negative effect arises from the fact that rearward-traveling light entering the optical path from the front side of the headgear may encounter an interface (e.g. an interface between a surface of a cover plate and air) and may thus be reflected frontward. This reflected light may then encounter another interface so that at least some of this light is re-reflected rearward. (By way of a specific example, incoming light that is reflected forwardly from front surface 301 of rear cover plate 300 may then be reflected rearwardly from rear surface 604 of switchable shutter 10.) In cases where the switchable shutter and the cover plate(s) are all essentially planar and parallel to each other, most or all of such reflected and then re-reflected light rays may follow the same path so any effect on the image seen by the wearer may be negligible. However, consideration of FIG. 3 reveals that when at least some of the optical components are curved, any such reflected and re-reflected light may be at least slightly offset from the path followed by incoming light that passed directly through without being reflected and re-reflected. This may result in the wearer of the headgear perceiving e.g. a double image or a blurred image, rather than a single, crisp image. Such potential problems may be again compounded by the presence of multiple air-solid interfaces from which such reflection and re-reflection can take place.

While such optical phenomena may not necessarily be unacceptable to the functioning of the protective headgear, it has been found that including at least two antireflective layers in the optical path may significantly enhance the viewing experience of a wearer of a protective headgear that includes a curved switchable shutter. Thus as disclosed herein, protective headgear 68 may comprise at least two antireflective layers, each antireflective layer being disposed on a major front surface or major rear surface of the rear cover plate, a major front surface or major rear surface of the front cover plate, or a major front surface or major rear surface of the curved switchable shutter.

Possible locations for antireflective layers are pointed out with reference to FIGS. 2 and 3. In these Figures, shutter 10 is sandwiched (along a generally forward-rearward optical path) between front cover plate 400 and rear cover plate 300. Front cover plate 400 comprises a major front surface 401 and a major rear surface 404. Major rear surface 404 of front cover plate 400 is spaced forwardly apart from major front surface 601 of shutter 10 so as to establish forward air gap 402 therebetween. Rear cover plate 300 comprises a major front surface 301 and a major rear surface 304. Major front surface 301 of rear cover plate 300 is spaced rearwardly apart from major rear surface 604 of shutter 10 so as to establish rearward air gap 302 therebetween.

With reference to FIG. 4, in some embodiments an antireflective layer 320 is provided on major rear surface 304 of rear cover plate 300. Antireflective layer 320 exhibits a major front surface 321 that faces forward toward rear cover plate 300 (and may be, but does not necessarily have to be, in direct contact with major rear surface 304 of rear cover plate 300.) Antireflective layer 320 exhibits a major rear surface 322 that faces toward the head of a wearer of the headgear. In some embodiments, an antireflective layer 340 is provided on major front surface 301 of rear cover plate 300. Antireflective layer 340 exhibits a major front surface 341 that faces forward toward rearward air gap 302 and shutter 10. Antireflective layer 340 exhibits a major rear surface 342 that faces rearward toward rear cover plate 300. In various embodiments an antireflective layer may be present only on a major front surface, or only on a major rear surface, of a rear cover plate. In other embodiments a rear cover plate 300 may comprise antireflective layers 320 and 340 respectively on rear and front surfaces thereof, as in the exemplary arrangement of FIG. 4.

With reference to FIG. 5, in some embodiments an antireflective layer 420 is provided on major rear surface 404 of front cover plate 400. Antireflective layer 420 exhibits a major front surface 421 that faces forward toward front cover plate 400. Antireflective layer 420 exhibits a major rear surface 422 that faces toward frontward air gap 402 and shutter 10. In some embodiments, an antireflective layer 440 is provided on major front surface 401 of front cover plate 400. Antireflective layer 440 exhibits a major front surface 441 that faces forward e.g. toward a source of high intensity light (e.g. from a welding operation). Antireflective layer 440 exhibits a major rear surface 442 that faces rearward toward front cover plate 400. In various embodiments an antireflective layer may be present only on a major front surface, or only on a major rear surface, of front cover plate 400. In some embodiments front cover plate 400 may comprise antireflective layers 420 and 440 respectively on rear and front surfaces thereof, as in the exemplary arrangement of FIG. 5.

Figure 6:
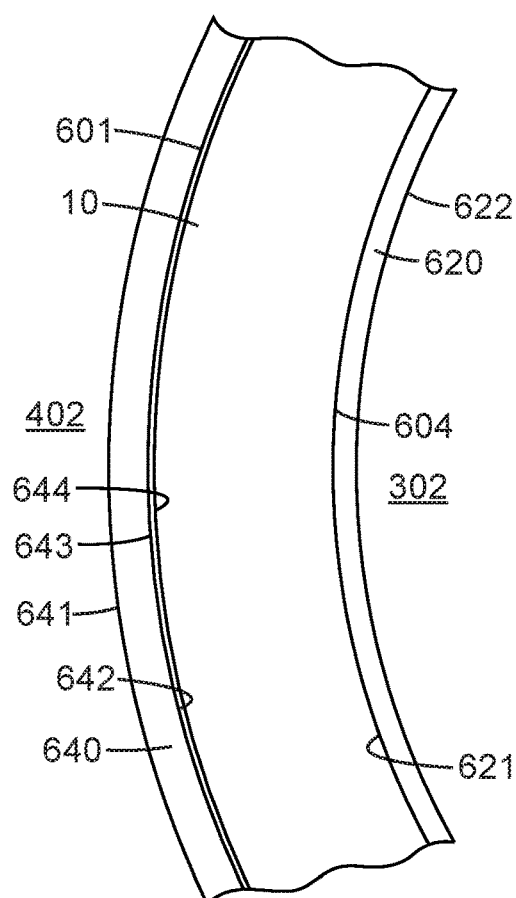
FIG. 6 is an isolated top view of an exemplary curved, switchable shutter comprising an antireflective layer on a front side thereof and an antireflective layer on a rear side thereof.

With reference to FIG. 6, in some embodiments, an antireflective layer 620 is provided on major rear surface 604 of shutter 10. Antireflective layer 620 exhibits a major front surface 621 that faces forward toward shutter 10. Antireflective layer 620 exhibits a major rear surface 622 that faces toward rearward air gap 302 and rear cover plate 300. In some embodiments, an antireflective layer 640 is provided on major front surface 601 of shutter 10. Antireflective layer 640 exhibits a major front surface 641 that faces forward toward forward air gap 402 and front cover plate 400. Antireflective layer 640 exhibits a major rear surface 642 that faces rearward toward shutter 10. In various embodiments an antireflective layer may be present only on a major front surface, or only on a major rear surface, of shutter 10. In other embodiments shutter 10 may comprise antireflective layers 620 and 640 respectively on rear and front surfaces thereof, as in the exemplary arrangement of FIG. 6.

Any combination of at least two of any of the above locations for antireflective layers may be chosen. In some embodiments, the optical path comprises a total of two antireflective layers. In some embodiments the two layers are on opposite major surfaces of the same optical component (e.g. a cover layer or a switchable shutter). In other embodiments, the two layers are on major surfaces of different optical components (e.g., a cover layer and the shutter). In some embodiments, the optical path comprises a total of three antireflective layers. In some embodiments two of the three layers are on opposite major surfaces of the same optical component (e.g. a cover layer), with a third being on a major surface of some other optical component (e.g., the shutter or the other cover layer). In other embodiments the three layers are on major surfaces of different optical components. In some embodiments, the optical path comprises a total of four antireflective layers. In some embodiments two of the four antireflective layers are on opposite major surfaces of one optical component and two of the antireflective layers are on opposite major surfaces of another optical component. In other embodiments two of the four antireflective layers are on opposite major surfaces of one optical component, a third is on a major surface of another optical component, and a fourth is on a major surface of still another optical component. In some embodiments the optical path comprises a total of five or six antireflective layers.

In some embodiments, antireflective layers are provided on the front and rear surfaces of the rear cover plate and no antireflective layer is present on either surface of the front cover plate. In other embodiments, antireflective layers are provided on the front and rear surfaces of the rear cover plate and also on the front and rear surfaces of the front cover plate. In some embodiments, no antireflective layer is present on the front surface of a front cover plate. In some embodiments, no antireflective layer is present on the rear surface of the front cover plate. In some embodiments, no antireflective layer is present on the front surface of the curved, switchable shutter. In some embodiments, no antireflective layer is present on the rear surface of the curved, switchable shutter. In some embodiments, no antireflective layer is present on the front surface or rear surface of the curved, switchable shutter. In some embodiments, an antireflective layer is present on the rear surface of the shutter but no antireflective layer is present on the front surface of the shutter. In particular embodiments, the rear cover plate comprises antireflective layers on its front and rear surfaces and the shutter comprises an antireflective layer on its rear surface, for a total of three antireflective layers in the optical path.

Although for brevity every possible combination of two, three, four, five or six antireflective layers may not be described individually herein, it is specifically noted that any desired combination of any such number and location of antireflective layers listed herein, can be used. For purposes of counting the number of antireflective layers present in the optical path of a protective headgear, two (or more) antireflective layers that are present on the same major surface of an optical component (i.e., a cover layer or a switchable shutter) will be counted as a single antireflective layer.

An antireflective layer is defined herein as a layer that, when present on or at a major surface of a substrate of an optical component of a protective headgear (e.g. a polycarbonate cover plate, a glass layer of a switchable shutter, etc.), reduces the reflection of light at a wavelength of approximately 520 nm by a factor of at least three (this and all related optical properties mentioned herein are measured at 0° incidence). Some antireflective layers are capable of reducing the reflected light to a considerably greater extent, and some are capable of broadband reduction of reflected light across a significant portion of the visible spectrum (of roughly 400-700 nm). In various embodiments, an antireflective layer when present on or at a major surface of a substrate of an optical component of a protective headgear, will reduce the reflection of light at a wavelength of 520 nm by a factor of at least about 4, 8, 16, or 32. In various specific embodiments, an antireflective layer when applied to a glass substrate with a refractive index of approximately 1.52, exhibits a percent reflection at a wavelength of 520 nm of less than about 2.0, 1.5, 1.0, 0.8, 0.6, 0.4, 0.2, or 0.1. (The performance of an antireflective layer on a glass substrate is provided herein for the purpose of gauging the optical characteristics of such an antireflective layer and does not require that such a layer, when used in a protective headgear, must be provided on a glass substrate.) In further specific embodiments, an antireflective layer may be a relatively broadband antireflective layer that exhibits a % reflection (on a glass substrate with RI approximately 1.52) at 450 nm and at 650 nm, of less than about 2.0, 1.5, 1.0, 0.8, 0.6, 0.4, or 0.2. By definition, an antireflective layer is optically transparent. In various embodiments, an antireflective layer may exhibit a spectral transmittance at 520 nm of at least about 90, 92, 94, 96, or 98%.

Any suitable antireflective layer may be used, of any suitable optically transparent composition, whether a single layer or comprising multiple sublayers. In general, antireflective layers often serve to reduce the refractive index mismatch between a solid substrate (e.g. glass, with an RI of about 1.52, or polycarbonate, with an RI of about 1.60) and air (with a refractive index of 1.0). In addition to this, or instead of this, antireflective layers often rely on destructive interference of reflected light waves. In such approaches an antireflective layer is provided with a refractive index and a physical thickness (which combine to form an optical thickness as is well known) that is approximately a quarter-wavelength of the wavelength of light for which it is desired to minimize reflections. Destructive interference of the light rays reflected from the front and rear surfaces of the antireflective layer can significantly reduce the amount of reflected light, in a manner that is well known. Any antireflective layer that is used in a protective headgear as disclosed herein, can rely on either or both of a refractive index-matching mechanism and a destructive-interference mechanism. Antireflective layers often rely on e.g. a low-refractive-index (RI) material (such as e.g. $MgF_2$, with an RI in the range of approximately 1.38), whether used alone or in combination with one or more higher-RI materials such as $TiO_2$ (with an RI e.g. in the range of approximately 2.3), $SiO_2$, $ZrO_2$, and so on.

In some embodiments, an antireflective layer may take the form of a single layer of a transparent material having a refractive index that is less than that of the substrate on which the material is provided. Any suitable material may be used, whether e.g. an inorganic material that is deposited e.g. by thermal evaporation methods, or a low-RI organic polymer (e.g. an organic polymeric material comprising e.g. fluorinated moieties) that is e.g. solvent-coated. By way of a specific example, a quarter-wave layer of $MgF_2$ when applied to a glass substrate with a refractive index of approximately 1.52, will reduce the reflected light from a level of about 4.3% to a level of about 1.3% (at a wavelength in the range of 520 nm). In specific embodiments, at least one antireflective layer as disclosed herein is a single layer of material that exhibits a refractive index of less than about 1.50 or less than about 1.40.

In some embodiments, an antireflective layer may comprise two sublayers, e.g. with indices of refraction less than that of the substrate on which they are provided, with the sublayers arranged e.g. in order of decreasing index of refraction from the substrate outwards. In other two-layer embodiments, a layer closest to the substrate may be a relatively high-RI layer (e.g. with an RI greater than that of the substrate) with an optical thickness less than a quarter-wave at the desired wavelength, followed by a relatively low-RI layer with an optical thickness greater than a quarter-wave.

In some embodiments, an antireflective layer may comprise three sublayers. In some embodiments such a layer may comprise e.g. a first sublayer (closest to the substrate) with a medium RI that is higher than that of the substrate and an optical thickness about a quarter-wavelength, a second layer with a higher RI and an optical thickness of about a half-wavelength, and a third layer with a low RI and with an optical thickness of about a quarter-wavelength. Variations on such approaches exist. In various specific embodiments, at least one antireflective layer as disclosed herein is a multi-sublayer stack comprising two or three sublayers of materials that differ from each other in refractive index by at least about 0.3, 0.5, 0.6, or 0.9.

In some embodiments, an antireflective layer may comprise four sublayers. Such four-sublayer constructions may comprise e.g. alternating higher and lower refractive index materials. Such approaches may often rely on a low-RI material that is e.g. $MgF_2$ or $SiO_2$, in combination with a high-RI material chosen from e.g. $TiO_2$, $ZrO_2$, $HfO_2$, $Ta_2O_5$, $Nb_2O_5$ (or a mixture of any of these high-RI materials). The thickness of the four individual sublayers may be chosen as desired e.g. in view of the central wavelength and/or breadth of the light for which it is desired to minimize reflections. In variations of such approaches, at least one of the four sublayers may be a medium-refractive-index material (e.g. indium-tin oxide or doped indium-tin-oxide). In still further variations of such approaches, at least one of the four sublayers may be an at least somewhat light-absorbing material chosen from e.g. nickel oxide or nickel chromium oxide. Two, three, and four-sublayer antireflective coatings are discussed in detail e.g. in U.S. Pat. No. 6,074,730 to Laird, U.S. Pat. No. 3,432,225 to Rock, and U.S. Pat. No. 5,579,162 to Bjornard, all of which are incorporated by reference in their entirety herein. In various specific embodiments, at least one antireflective layer as disclosed herein is a multi-sublayer stack comprising at least four sublayers of materials that differ from each other in refractive index by at least about 0.3, 0.5, 0.6, or 0.9.

Figure 7:
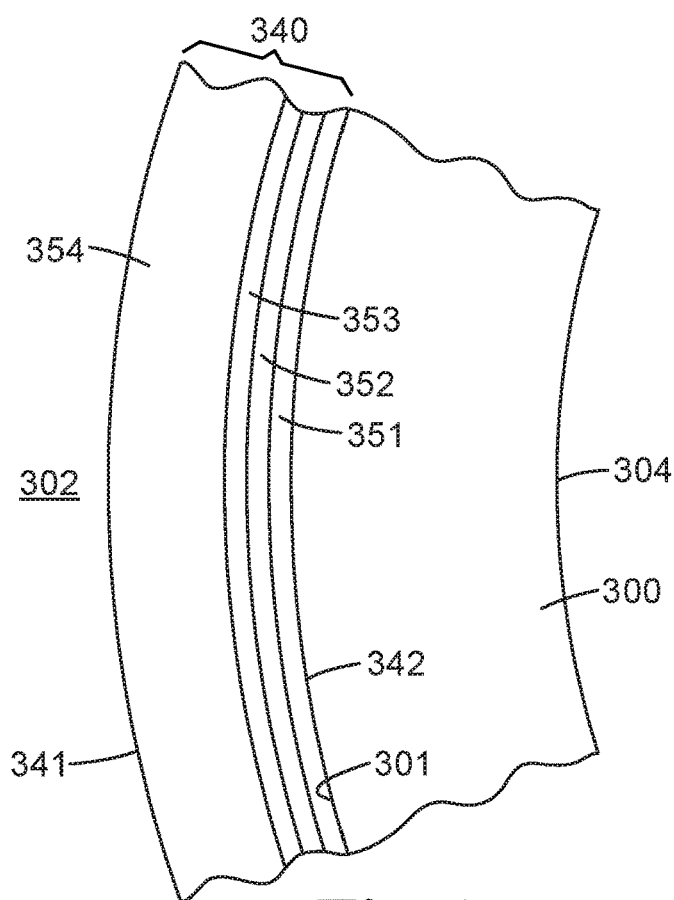
FIG. 7 is an isolated top view of an exemplary rear cover plate comprising a multilayer antireflective layer.

In the above discussions, a requirement that various sublayers have refractive indices that differ from each other does not mean that no two sublayers (e.g. out of four sublayers) are allowed to have the same refractive index. Rather, it means that any two nearest-neighbor sublayers will exhibit different refractive indices. Two sublayers that are not nearest neighbors may exhibit similar or the same refractive index and in fact may be made of the same material. Thus in some embodiments, an antireflective layer as disclosed herein may exhibit a four-sublayer arrangement of the general type disclosed in U.S. Pat. No. 3,235,397 to Millendorfer. With reference to the exemplary arrangement depicted in FIG. 7, such an antireflective layer (layer 340 of FIG. 7) can include four alternating sublayers chosen from high and low RI materials (e.g. $TiO_2$ and $MgF_2$) with a high-RI material providing first (closest to the substrate) sublayer 351 and third sublayer 353, and with a low-RI material providing second sublayer 352 and fourth (outermost) sublayer 354. In such embodiments, the high-RI sublayers can be, but do not have to be, the same material; similarly, the low-RI sublayers can be, but do not have to be, the same material. In particular embodiments the outermost (low RI) layer 354 can have an optical thickness (e.g. in the range of 140-180 nm) that is close to a quarter-wave of the light of interest, while the inner three layers may each have an optical thickness that is considerably less (e.g. in the range of 40-80 nm).

In further embodiments, an antireflective layer may include more than four sublayers. For example, five, six, seven, eight, ten, twelve, sixteen or more sublayers may be used. Many of the above approaches (regardless of the number of sublayers) share the common features of inorganic materials (such as various metal oxides, fluorides, and so on) with various high, low and/or intermediate refractive indices, and that are provided at physical thicknesses chosen in combination with their refractive indices to provide optical thicknesses as desired. Certain sublayers may be provided at quarter-wave thicknesses that center the maximum antireflectance of the sublayer stack at or near the wavelength of interest. Other sublayers may serve primarily to broaden the antireflection performance around this central wavelength of interest. Any such sublayers in any suitable combination, may be used in an antireflective layer as disclosed herein. Such materials may be e.g. sputter-coated, magnetron-coated, e-beam coated, DC-reactive-sputtered, and so on, as is well-known.

In some embodiments an antireflective layer may comprise an organic polymeric material that includes groups (e.g. fluorinated moieties) that reduce the refractive index of the material to a range that provides useful antireflective properties. Such materials may be deposited onto a major surface of a substrate e.g. by solvent coating (e.g., dip coating, spray coating, and so on). A single layer may be used; or, multiple layers (which may differ in refractive index) may be applied. Such materials and approaches are described in detail in U.S. Pat. No. 5,198,267 to Aharoni, which is incorporated by reference in its entirety herein.

The above discussions have primarily concerned additive approaches in which an antireflective sublayer is disposed on (e.g. by coating, lamination, etc.) a major surface of a substrate of an optical component. However, in some embodiments, an antireflective layer may be obtained by surface modification methods, some of which methods may be subtractive methods (e.g., etching, ablation, and the like) rather than additive methods. This being the case, the concept of an antireflective "layer" does not necessarily require that the layer must be a separately-added layer on a major surface of a substrate of an optical component. Rather, in some embodiments an antireflective layer may be a surface layer of such a substrate, which surface layer has been modified to provide an antireflective property.

Such surface modification methods may include any process that serves to modify the major surface of a substrate (e.g. from an original, e.g. optically smooth, condition) to impart a textured surface that exhibits features in a suitable size range and arrangement to reduce the refractive index mismatch at an interface between the solid substrate (e.g. a polycarbonate cover plate) and an adjoining material (e.g. the air of an air gap). The features should of course not unacceptably affect the quality of the transmitted image. Such features can have any suitable shape and arrangement, whether regular or irregular. Furthermore, they may be positive (protruding) features (achieved e.g. by additive approaches involving the deposition of materials (e.g., nanoparticles, etc.) atop the major surface of the substrate; or, they may be negative (recessed) features (achieved e.g. by subtractive approaches such as etching, ablation, etc.). Mixtures of positive and negative features may be present. Potentially suitable features include e.g. columns, pyramids, trenches, posts, valleys, grooves, channels, divots, so-called "moth-eye" structures, and so on. Such features may often have at least one characteristic dimension (e.g., protrusion height or cavity depth) in the submicron range, e.g. from about 20 nm to about 300 nm. As noted, above, such features may serve to reduce the abruptness of the transition in refractive index between the air and the substrate surface; such antireflective layers are often referred to as gradient-index layers. Subtractive methods (using e.g. plasma etching) of imparting antireflective surface layers to materials are described e.g. in U.S. Patent Application Publication No. 2015/0077854 to Yu, which is incorporated by reference in its entirety herein.

In some embodiments such features may be achieved directly e.g. by molding a cover plate in an injection molding cavity comprising molding surfaces that have been machined to have the negative of the pattern to be imparted to the major surfaces of the molded cover plate. An antireflective layer (whether an antireflective surface layer, an additive layer, etc.) need not be present over the entirety of a major surface of a substrate of an optical component such as cover plate or of a glass plate of a switchable shutter. Rather, the layer need only be present over all areas that are in the optical path; it may not necessarily be present e.g. along perimeter areas that are optically blocked when the cover plates and shutter are assembled into the headgear.

As discussed above, in some embodiments an antireflective surface layer may be a major surface of a substrate of an optical component (e.g. a polycarbonate cover plate or a glass plate of a switchable shutter). In other embodiments an antireflective surface layer may be a major surface of a layer of material that is specifically chosen for its ability to have surface antireflective properties imparted thereto (whether by way of an additive process or a subtractive process). Such a layer may be e.g. bonded or laminated to an optical component by any of the methods disclosed below (e.g. by use of an optically clear adhesive). Or, it may be disposed on a major surface of at least a portion of a substrate e.g. by film-insert-molding.

Thus in general, an antireflective layer that is disposed on a major surface of an optical component may be, but does not necessarily have to be, in direct contact with the major surface of the optical component. For example, in some embodiments an antireflective layer may be disposed on a major surface of a cover plate by way of being deposited (e.g. by sputtering) on a major surface of a layer (such as e.g. a hardcoat) that is on cover plate. Or, in some embodiments an antireflective layer may be provided on a first major side of a carrier layer (e.g. a polymeric film). For example, in some embodiments an antireflective layer may be deposited onto a first major surface of a polymeric film carrier layer (or, a major surface of the carrier layer may be e.g. embossed, etched, or ablated, to comprise an antireflective surface layer). The second major surface of the carrier layer may then be bonded (e.g. via an optically clear adhesive such as an optically clear pressure-sensitive adhesive) to a major surface of an optical component such as a cover plate or a switchable shutter. For example, FIG. 6 illustrates an exemplary arrangement in which an antireflective layer 640 is disposed on a surface of a carrier layer 643 that is bonded to major surface 601 of switchable shutter 10 by an optically clear pressure-sensitive adhesive 644.

In such embodiments, a carrier layer (and an optically clear adhesive) may be chosen (taking into account both their thickness and their refractive index) to minimize any undesirable effect that they might have on the performance of the antireflective layer. Potentially suitable optically clear adhesives include the products available from 3M Company under the trade designations 3M OPTICALLY CLEAR ADHESIVES 8211, 8212, 8213, 8214, and 8215.

For purposes of determining the number of antireflective layers present in the optical path of a protective headgear, all antireflective layers (whether single-layer, or multi-sublayer arrangements) that are on the same surface of an optical component will be considered to be a single antireflective layer. This is whether the antireflective layers (or sublayers thereof) are in direct contact with each other or are separated e.g. by a layer that is substantially optically inert (e.g. a layer with a half-wave optical thickness). By definition, air gaps, cover plates (of e.g. polycarbonate), and glass plates (e.g. of a switchable shutter), are not optically inert layers. Furthermore, an antireflective layer (whether an antireflective surface layer, an additive layer, etc.) need not be present over the entirety of a major surface of a substrate of an optical component (such as e.g. a front or rear cover plate, or a front or rear glass cover sheet of a switchable shutter). Rather, the layer need only be present over all areas that are in the optical path; it may not necessarily be present e.g. along perimeter areas that are optically blocked when the cover plates and shutter are assembled into the headgear.

Figure 8:
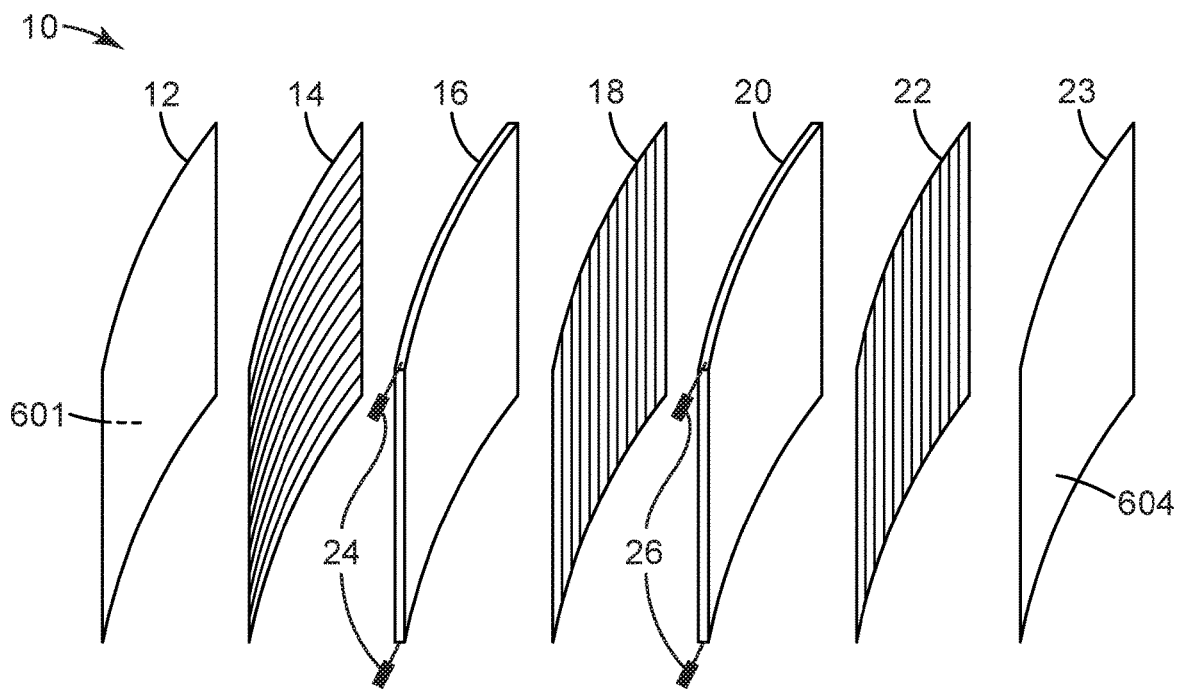
FIG. 8 is an exploded isolated side perspective view of components of an exemplary curved, switchable shutter.

FIG. 8 shows an exploded view of an exemplary curved, switchable, shutter 10 that can be used in an automatic darkening filter 60. In some embodiments, a frontmost (e.g., passive) component of the shutter 10 is a band pass filter 12 that serves to attenuate the infra-red (IR) and ultra-violet (UV) wavelength components from a high-intensity incident light. The band pass filter 12 can be an interference filter that reflects the IR radiation and absorbs the UV-A, -B and -C components of the incident light. The band pass filter 12 also may be a combination of separate IR and UV reflecting and/or absorbing filters. In many embodiments, such a band pass filter may comprise a flexible sheet (of e.g. 0.1 mm in thickness) upon which various layers may be deposited to form the interference filter. Such a sheet may provide the frontmost structural component of shutter 10 and thus may serve as a flexible front cover sheet for shutter 10. A front surface of the flexible front cover sheet (or of a layer provided thereon, e.g. a hardcoat) may thus provide major front surface 601 of shutter 10. In some embodiments a flexible front cover sheet of shutter 10 may be comprised of flexible glass. In other embodiments, a flexible front cover sheet of shutter 10 may be made of a flexible organic polymeric material (chosen from e.g. polycarbonate, polyimide, polyolefin, polycarbonate, polyethylene naphthalate, or cellulose triacetate) that exhibits a suitable combination of mechanical and optical properties. In some embodiments shutter 10 may comprise a separate flexible front cover sheet (made e.g. of any of the above materials) that is positioned in front of band pass filter 12.

The curved, switchable shutter 10 also includes a first polarization filter 14, a first optically-rotating liquid-crystal cell 16, and a second polarization filter 18. The polarization filters 14 and 18 have substantially orthogonal polarization directions, where the polarization direction of the first polarization filter 14 is approximately 90° to the polarization direction of the second polarization filter 18 but in a parallel place. The first optically-rotating, liquid-crystal cell 16 may be a twisted, nematic, liquid-crystal cell located between the first and second orthogonally-related polarization filters 14 and 18. In parallel alignment with these components is a second liquid-crystal cell 20, disposed between a pair of polarization filters 18 and 22. The polarization filters 18 and 22 each have substantially parallel polarization directions. The parallel polarization directions enable the cell to be dark when no voltage is applied and light when there is voltage. The default dark-state provides a safety function that notifies the user that the product is turned "off". Each of the liquid crystal cells 16 and 20 are provided with connectors 24 and 26, respectively, by which control voltages can be applied to these cells. The application of a voltage to connectors 24 creates an electric field between the flexible layers of the liquid-crystal cell 16. The nematic, liquid-crystal molecules align with the electric field perpendicular to the defining surfaces that enclose the major sides of the cell. This perpendicular alignment, rather than a parallel one, in the excited cell achieves a darkened state. Thus, when a control voltage is applied to the liquid-crystal cell 16, a filter effect is achieved. The liquid-crystal cell controls the polarization of the light, and the light becomes absorbed by the polarizer. The degree of rotation of the nematic molecules may be controlled by varying the control voltage, and thus the corresponding filter effect also may be controlled. The result is that the liquid-crystal cell 16 is in a light transmission state in the absence of an applied voltage and is in a dark transmission state in the presence of the applied voltage. The voltage levels may be different for varying cell designs, depending on the liquid crystal materials used, cell gap geometries, etc. In various embodiments, the light transmission state may corresponds to any of welding shades 2 to 4, and the dark transmission state, which can be user-selectable, can correspond to any of welding shades 7 to 14. The welding shades have been defined in eye protection standards ANSI Z87.1:2015 and EN 169:2001.

Figure 9:
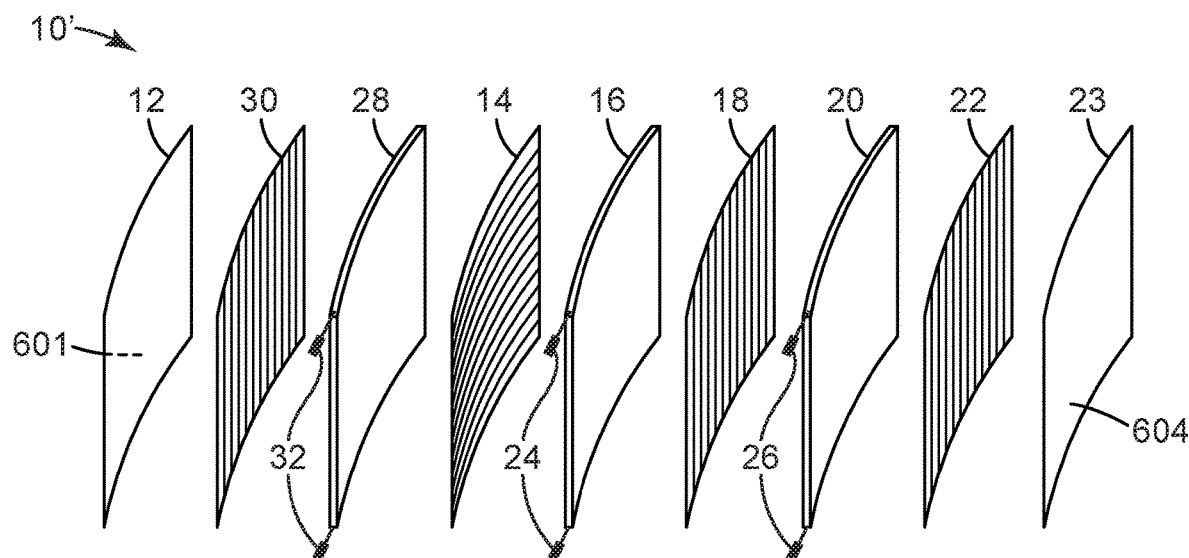
FIG. 9 is an exploded isolated side perspective view of components of another exemplary curved, switchable shutter.

FIG. 9 shows an exploded view of a switchable shutter 10' in an alternative embodiment. Shutter 10' comprises liquid-crystal cells 16, 20, and 28. The first liquid-crystal cell 16 is disposed between the first and second polarization filters 14 and 18, the second liquid-crystal cell 20 is disposed between first and third polarization filters 18 and 22, and the third liquid-crystal cell 28 is disposed between polarization filters 30 and 14. The two liquid crystal cells 16 and 28 may be substantially identical, but they are generally rotated about 180° with respect to each other, to give less optical variation for different viewing angles. The application of a voltage to connectors 24 and 32 creates an electric field between transparent conductive electrodes. The nematic, liquid-crystal molecules align with the electric field perpendicular to the surfaces that enclose the molecules to cause the cells to restrict light transmission. The alignment directions of the liquid crystal cells 16 and 28 are arranged substantially parallel to and oriented asymmetrically with respect to one another. The advantages of positioning two substantially-identical, liquid-crystal cells together, such that the face-to-face molecule alignment directions are substantially perpendicular, compensates for an angular dependency of the filtering effect. Variations in shade (improved homogeneity) in the dark state may be achieved using offset polarizers, that is polarizers offset by about 1 to 20 degrees—see U.S. Pat. No. 7,884,888 to Magnusson et al. The offset polarizers may eliminate an uneven shade of the viewing area caused by variations in cell-gap geometry, unwanted birefringence in the adhesive layers of the construction, and different viewing angles.

Figure 10:
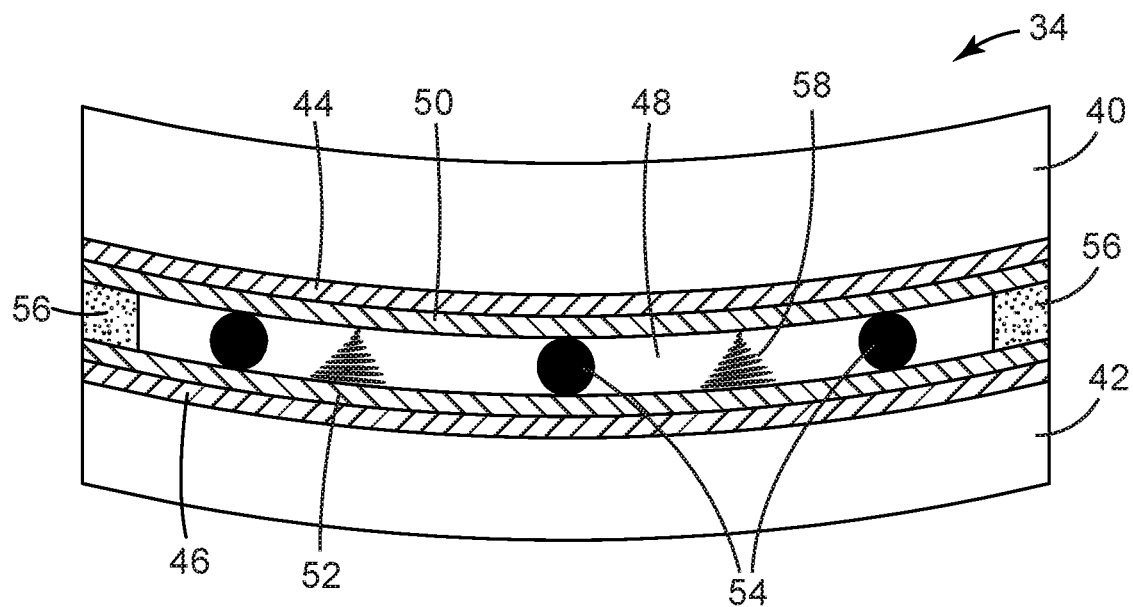
FIG. 10 is a schematic cross-sectional view of an exemplary curved liquid-crystal cell.

FIG. 10 shows a liquid-crystal cell 34 such as any of the first, second, and third cells 16, 20, and 28. The laminar construction contains two optically-transparent flexible layers 40 and 42. A liquid-crystal cell can be implemented using a variety of such layers, made of e.g. glass or of any suitable organic polymeric film. The thickness of each of the layers may be about 10 micrometers (μm) to 200 μm, more typically about 30 to 150 μm, and still more typically about 75 to 125 μm. The flexible layers 40 and 42 may be supplied in sheet or roll form. The curved layers 40, 42 typically have a radius of less than infinite curvature, typically about 5 to 30 centimeters (cm), more typically about 7 to 20 cm. The curvature also may exhibit a non-constant radius, for example, it may be parabolic, catenary, epicycloidal, and free form.

On the inwardly facing surfaces of the optically-clear layers 40 and 42 are transparent conductive electrode layers 44 and 46, respectively, (e.g., indium tin oxide layers). By applying a voltage to the electrodes 44 and 46, an electric field is created across the liquid-crystal layer 48 to shift the orientation of the liquid crystal molecules. Juxtaposed against the electrodes 44 and 46 are alignment layers 50 and 52, respectively, for instance, a polyimide layer that has been treated mechanically, such as by brushing or rubbing, in specific alignment directions. The alignment layers 50 and 52 are spaced apart using equally sized spacers 54, inside the cells. The cell edges can be sealed using an edge adhesive 56, such as Norland 68, available from Norland Products, Cranbury, N.J. Before the cell is completely sealed, the nematic molecules 58 are pumped into the gap between the layers 50 and 52 to form liquid-crystal layer 48. The alignment layers 50 and 52 force the liquid-crystal nematic molecules 58 to take specific angular positions at the surfaces so that the molecules are twisted through their respective twist angle between these surfaces. The rotational condition of the nematic liquid-crystal 58 permits or blocks light-transmission through the cell. The liquid crystals used may be of the nematic type with a Δn (difference between the refractive index of ordinary and extraordinary light rays) of e.g. about 0.08 to 0.14 sandwiched between the two optically-clear flexible layers 40 and 42. The gap between layers 50 and 52 typically is about 3-5 μm. The optically-transparent flexible layers 40 and 42 used in the present invention generally have a substantially-uniform optical transmission, typically greater than 80% in the wavelength range of 380 nanometers (nm) to 750 nm. If comprised of glass, the layers may be formed by an overflow downdraw method to have a thickness as indicated above. The composition of a glass layer may be various glass compositions of silicate glass and the like, such as silica glass and borosilicate glass. A non-alkali glass may include glass that does not substantially contain an alkali component, specifically, glass containing an alkali metal oxide of 1000 parts per million (ppm) or less (preferably, of 500 ppm or less, and more preferably, of 300 ppm or less). Such a glass layer may have a protective sheet juxtaposed against it. When winding the glass layer, the protective sheet prevents occurrence of the flaws, which is caused by contact of one part of the glass layer with another. The protective sheet absorbs external pressure applied to the glass roll. The thickness of the protective sheet may be from 10 μm to 2000 μm. The protective sheet may be an ionomer film, a polyethylene film, a polypropylene film, a polyvinyl chloride film, a polyvinylidene chloride film, a polyvinyl alcohol film, a polypropylene film, a polyester film, a polycarbonate film, a polystyrene film, a polyacrylonitrile film, an ethylene vinyl acetate copolymer film, an ethylenevinylalcohol copolymer film, an ethylene-methacrylic acid copolymer film, a nylon film (polyamide film), a polyimide film, cellophane or other buffer materials made of resins. Conductivity may be imparted to the protective sheet by adding a component for imparting the same, such as polyethylene glycol, into the protective sheet. In a case where the protective sheet is made of inserting paper, it is possible to impart the conductivity by adding conductive fiber. Further, it is possible to impart the conductivity also by laminating a conductive layer, such as an indium-tin-oxide (ITO) film, on a surface of the protective sheet. Examples of commercially-available flexible glasses include Schott D263T glass. As noted above, in some embodiments, a liquid crystal cell may be use suitable flexible organic polymeric materials (e.g., plastic sheeting) rather than flexible glass.

Liquid crystal cells 16, 20, and 28 may be a twisted, nematic, liquid-crystal cell type cell that provides a "fail-safe" intermediate transmission state in the case of electronic module failure. An automatic darkening filter that has low-twist, liquid-crystal, cells is described in U.S. Pat. No. 6,097,451 to Palmer et al.; see also U.S. Pat. No. 5,825,441 to Hornell et al. The twisted, nematic, liquid-crystal cell may have a twist angle of less than 100 degrees, typically zero or 1 to 99 degrees. The liquid-crystal cell also may have a low twist angle of 1 to 85 degrees. More specifically, the twist angle of a low-twist, liquid-crystal, cell may be about 30 to 70 degrees. A "fail-safe" liquid crystal cell is in many ways similar in design to the low-twist, liquid-crystal, cell, but its operation is different because it is sandwiched between parallel polarizers, as opposed to crossed or orthogonal polarizers. Liquid crystal cell 20 is in a dark transmission state (a nearly optically-opaque state in which the majority of the incident light is blocked) when no voltage is applied to the connectors 26. Liquid crystal cell 20 may become optically transparent when a certain voltage is applied.

Switchable shutters of the present invention may be curved about one, two, or three axis. Typically a switchable shutter used in a welding helmet would be curved about one or two axes, e.g. about a vertical axis. At the very least, a switchable shutter will be curved (arcuate) along at least a portion of its lateral extent (i.e., curved with respect to a vertical axis) when viewed in a top view (as in FIG. 3). The front and rear cover plates may be likewise curved with respect to a vertical axis. In various embodiments the front and rear cover plates may exhibit generally, substantially, or essentially identical curvature to each other. In some embodiments, one of the cover plates may exhibit a more pronounced curvature (i.e. a smaller radius of curvature at a corresponding location along the lateral extent of the cover plates) than the other cover plate. In various embodiments one or both cover plates may be curved to be congruent with the curvature of the switchable shutter e.g. so that a generally, substantially or essentially constant air gap between the cover plate and the shutter exists. In some embodiments, the curvature of a cover plate may be such that the air gap varies e.g. along the lateral extent of the optical components. In various embodiments, the switchable shutter (and the front and rear cover plates) may exhibit readily identifiable curvature (e.g. corresponding to a radius of curvature of less than about 20 cm) along at least 20, 40, 80, or essentially 100% of its lateral extent when viewed in top view). The physical properties of the flexible layers may allow for curved switchable shutters to be manufactured which have a radius of curvature of e.g. about 5 cm to 20 cm, and a viewing area of about 10 to 600 square centimeters ($cm^2$), more typically 30 $cm^2$ to 250 $cm^2$. Conventional welding filters typically have a viewing area of about 50 to 100 $cm^2$. The present invention may enable switchable shutters having a viewing area of at least 100 $cm^2$ to 125 $cm^2$ to be provided.

Regardless of the specific number of polarizers, liquid-crystal cells, etc., in some embodiments a curved switchable shutter 10 will comprise a flexible rear cover sheet 23 that will be the rearmost structural component of shutter 10. A rear surface of cover sheet 23 (or a surface of a layer, e.g. a hardcoat, provided thereon) may thus provide major rear surface 604 of shutter 10, as in the exemplary embodiment of FIGS. 8 and 9. In some embodiments a flexible rear cover sheet may be provided by an item that serves an additional role in shutter 10 (e.g., in similar manner that a flexible front cover sheet can serve as a substrate for a band pass filter). For example, a suitable material may serve as a substrate of a polarization filter as well as a flexible rear cover sheet. In some embodiments, flexible rear cover sheet 23 may be made of glass e.g. with a thickness in the range of about 0.1 mm. In other embodiments, flexible rear cover sheet 23 may be made of a flexible organic polymeric material (chosen from e.g. polycarbonate, polystyrene, polyimide, polyolefin, polycarbonate, polyethylene naphthalate, cyclic olefin polymer, or cellulose triacetate) that exhibits a suitable combination of mechanical and optical properties.

The use of curved switchable shutters in protective headgear is discussed in detail in U.S. Patent Application Publication 2014/0013479 to Magnusson, which is incorporated by reference in its entirety herein.

Figure 11:
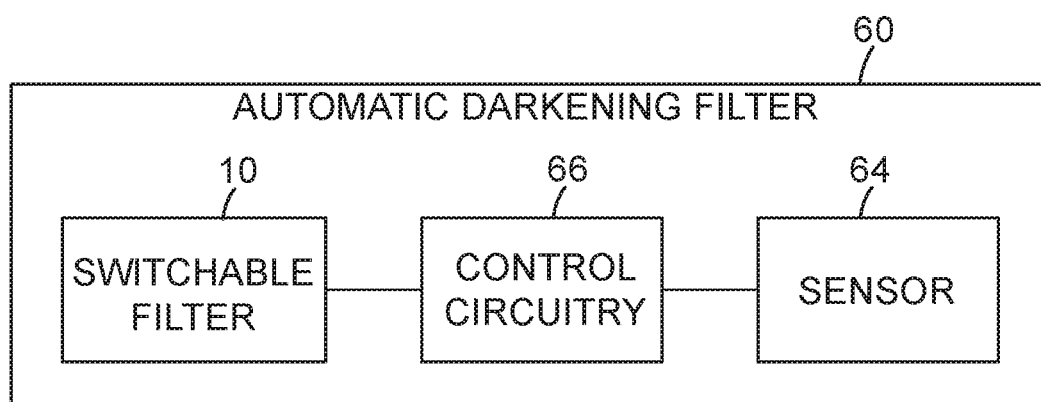
FIG. 11 is a block diagram of an exemplary automatic darkening filter.

FIG. 11 is a block diagram of an automatic darkening filter (ADF) 60. Automatic darkening filter 60 includes a curved switchable shutter 10 (or 10') that may comprise e.g. offset polarizers of the type described above with respect to FIGS. 8 and 9. Switchable shutter 10 is mounted in protective headgear 68 that would be worn by the user during a welding procedure or other situation where protection of the type provided by switchable shutter 10 is desired. ADF 60 also includes a sensor 64 for detecting light incident upon the front surface of shutter 10, such as a welding arc. The sensor detects incident light and causes a signal to be sent which causes molecular rotation within the liquid crystal layer. Sensor 64 thus may be capable of detecting at least an input from the presence of high intensity light. Such a sensor may be located physically close to some or all of the other components (hardware, etc.) of automatic darkening filter 60 or may be located physically remote from some or all of these components. Such a sensor may use any suitable sensing mechanism, chosen from e.g. various photodetector devices and technologies. The sensor 64 may be provided with a polarizing member that precludes non-normal light from activating the sensor. Such a device prevents light from other welding torches and sensors from reaching the sensor—see U.S. Pat. No. 6,934,967 to Migashita et al.

Control circuitry 66 receives signals from the sensor 64 pertaining to the presence or absence of incident light and causes corresponding control voltages to be applied to shutter 10, thus controlling the degree of shade provided by shutter 10. Control circuitry 66 may take the form of e.g. an electronic control unit for receiving and controlling the various signals to switchable shutter 10 and, more particularly, liquid crystal cells (e.g., 16, 20 and 28) thereof, e.g. by way of connectors 24, 26 and 32, respectively. When the presence of a welding arc or other source of incident light is detected by sensor 64, for example, control circuitry 66 may cause a control voltage to be applied to liquid-crystal cells 16 and 20 while eliminating the voltage to guest-host cell 28. This causes the shutter 10 to darken and protect the user from the glare of the incident light. In the absence of a welding arc or other source of incident light, control circuitry 66 may reduce or eliminate the applied voltage to liquid crystal cells 16 and 20, thus causing the shutter to become more open to light. This increase in light transmittance enables a welder, for example, to perform a welding operation and also to perform tasks outside the welding area without removing the protective facemask or helmet. In addition, the filter construction described herein results in increased homogeneity in the dark state as seen by the user over a large angular range.

In some embodiments, one or more surfaces of a substrate of an optical component (e.g. a front or rear cover plate or a curved, switchable shutter) may comprise a hardcoat, in order to, for example, enhance the abrasion resistance of the substrate. Such a hardcoat may be particularly useful if a substrate (e.g., a front or rear cover plate; or, a flexible front cover sheet or a flexible rear cover sheet of the switchable shutter) is an organic polymeric material rather than e.g. glass. If a hardcoat is present on a surface on which an antireflective layer to be provided, in at least some embodiments the hardcoat may be positioned inwardly (toward the substrate, i.e., sandwiched between the substrate and the antireflective layer) so as to minimize any disruption of the antireflection achieved by the antireflective layer. (In other words, an antireflective layer may be deposited atop the hardcoat, with the hardcoat effectively serving as part of the substrate of the optical component.)

In some embodiments, at least a rear surface of a rear cover sheet 23 of shutter 10 may include a hardcoat thereon. In some embodiments, at least a front surface of a glass substrate of bandpass filter 12 of shutter 10 may include a hardcoat thereon. Hardcoats are widely known and may be chosen from any suitable recipe or composition, deposited on the substrate in any suitable manner. Hardcoats often contain inorganic oxide particles, e.g., silica, of nanometer dimensions dispersed in a binder precursor resin matrix, and sometimes are referred to as "ceramers". In particular embodiments, certain hardcoats may include components (e.g. particles of a particular size, e.g. nanoparticles) to impart optical effects. If such particles provide sufficient reduction in reflection that a hardcoat meets the criteria presented herein, the hardcoat may then be considered to be an antireflective layer as defined herein (of course, if an additional antireflective layer is applied onto the hardcoat layer, the combination of these will count as only one antireflective layer in view of the previous discussions herein).

In various embodiments, protective headgear 68 may take the form of e.g. a helmet, a shield, or a visor (e.g., a welding helmet, shield or visor), noting that there may not always be bright-line boundaries between protective headgear of these categories. By definition, a protective headgear as disclosed herein does not encompass eyewear such as e.g. goggles, vision-corrective eyeglasses, ordinary safety glasses sunglasses, that do not comprise an autodarkening filter. Such a helmet may comprise e.g. a head suspension that engages the wearer's head when the helmet is donned. Potentially suitable head suspensions are described e.g. in U.S. Pat. No. 8,505,121 to Lilenthal. In some embodiments, such a helmet may include a crown member that engages the wearer's head when headgear 68 is being donned, as described e.g. in U.S. Pat. No. 7,865,968 to Lilenthal et al. In some embodiments, the entire main body 70 of headgear 68 (including the portion to which the switchable shutter is mounted) may be rotatable with respect to a head suspension of the headgear. In some embodiments, the switchable shutter can be mounted to a portion (e.g. a visor portion) of the protective headgear that it is rotatable with respect to the main body of the headgear. The automatic darkening filter of the present invention can be used in connection with industrial operations, for example welding (e.g. arc welding, torch welding, acetylene welding), cutting (e.g. laser cutting, acetylene cutting), brazing, soldering and the like. They also can be used in connection with medical procedures involving high intensity light (e.g. laser surgery, hair removal, tattoo removal, light-curing of dental resins, etc.) and other uses as well.

This application is a continuation of U.S. patent application Ser. No. 16/096,939, now allowed, which was a national stage filing under 35 U.S.C 371 of PCT application No. PCT/US2017/031545, which claimed priority to U.S. Provisional Application No. 62/335,256, the disclosures of all of which are incorporated by reference in their entirety herein.

LIST OF EXEMPLARY EMBODIMENTS

Embodiment 1 is a protective headgear comprising: an automatic darkening filter that comprises a curved switchable shutter that exhibits a curvature; a front cover plate that exhibits a curvature and that is positioned in front of the shutter; and, a rear cover plate that exhibits a curvature and that is positioned in rear of the shutter, wherein the front and rear cover plates and the shutter define an optical path that electromagnetic radiation can follow to reach the eyes of a wearer of the protective headgear; and wherein the optical path comprises at least two antireflective layers, each antireflective layer being disposed on a major front surface or major rear surface of the rear cover plate, a major front surface or major rear surface of the front cover plate, or a major front surface or major rear surface of the curved switchable shutter.

Embodiment 2 is the protective headgear of embodiment 1 wherein the optical path comprises at least one antireflective layer, that is on a major front surface or a major rear surface of the rear cover plate. Embodiment 3 is the protective headgear of any of embodiments 1-2 wherein the optical path comprises at least one antireflective layer, that is on a major front surface or a major rear surface of the curved switchable shutter. Embodiment 4 is the protective headgear of any of embodiments 1-3 wherein the optical path comprises at least one antireflective layer, that is on a major front surface or a major rear surface of the front cover plate. Embodiment 5 is the protective headgear of any of embodiments 1-4 wherein the optical path comprises an antireflective layer on the major rear surface of the rear cover plate and an antireflective layer on the major front surface of the rear cover plate. Embodiment 6 is the protective headgear of any of embodiments 1-5 wherein the optical path comprises an antireflective layer on the major rear surface of the rear cover plate and an antireflective layer on the major rear surface of the curved switchable shutter. Embodiment 7 is the protective headgear of any of embodiments 1-6 wherein the optical path comprises an antireflective layer on the major rear surface of the rear cover plate, an antireflective layer on the major front surface of the rear cover plate, and an antireflective layer on the major rear surface of the curved switchable shutter.

Embodiment 8 is the protective headgear of any of embodiments 1-7 wherein the optical path comprises an antireflective layer on the major rear surface of the rear cover plate, an antireflective layer on the major front surface of the rear cover plate, and an antireflective layer on a major front surface or a major rear surface of the front cover plate. Embodiment 9 is the protective headgear of any of embodiments 1-8 wherein the optical path comprises an antireflective layer on the major rear surface of the rear cover plate, an antireflective layer on the major front surface of the rear cover plate, an antireflective layer on the major rear surface of the front cover plate, and an antireflective layer on the major front surface of the front cover plate. Embodiment 10 is the protective headgear of any of embodiments 1-9 wherein the optical path comprises an antireflective layer on the major rear surface of the rear cover plate, an antireflective layer on the major front surface of the rear cover plate, an antireflective layer on the major rear surface of the curved switchable shutter, an antireflective layer on the major rear surface of the front cover plate, and an antireflective layer on the major front surface of the front cover plate.

Embodiment 11 is the protective headgear of any of embodiments 1-10 wherein at least one of the antireflective layers is a single layer of material that exhibits a refractive index less than about 1.50. Embodiment 12 is the protective headgear of any of embodiments 1-11 wherein at least one of the antireflective layers is a multi-sublayer stack comprising two or three sublayers of materials that differ from each other in refractive index by at least about 0.3. Embodiment 13 is the protective headgear of any of embodiments 1-12 wherein at least one of the antireflective layers is a multi-sublayer stack comprising four sublayers of materials that differ from each other in refractive index by at least about 0.3. Embodiment 14 is the protective headgear of embodiment 13 wherein an outwardmost sublayer of the four sublayers exhibits a refractive index of at most about 1.5 and exhibits an optical thickness that is from about 80% to about 120% of the combined optical thickness of the other three sublayers.

Embodiment 15 is the protective headgear of any of embodiments 1-14 wherein at least one of the antireflective layers is disposed on a carrier layer that is adhered to a major surface of the front cover layer, the rear cover layer, or the curved, switchable shutter, by an optically clear adhesive. Embodiment 16 is the protective headgear of any of embodiments 1-15 wherein at least one of the antireflective layers is disposed on a major front surface of a flexible front cover sheet that is a frontmost structural component of the curved, switchable shutter, or is disposed on a major rear surface of a flexible rear cover sheet that provides a rearmost structural component of the curved, switchable shutter.

Embodiment 17 is the protective headgear of any of embodiments 1-16 wherein the curvature of the front cover plate is at least generally congruent with the curvature of the curved switchable shutter, and wherein the curvature of the rear cover plate is at least generally congruent with the curvature of the curved switchable shutter. Embodiment 18 is the protective headgear of any of embodiments 1-17 wherein the optical path includes a front air gap of from about 0.5 mm to about 4 mm between a major rear surface of the front cover plate and a major front surface of the curved, switchable shutter, and further includes a rear air gap of from about 0.5 mm to about 4 mm between a major rear surface of the curved, switchable shutter and a major front surface of the rear cover plate. Embodiment 19 is the protective headgear of embodiment 18 wherein the rear air gap of the optical path is between about 0.5 mm and about 2 mm and is at least substantially constant over a lateral extent of the rear air gap of the optical path.

Embodiment 20 is the protective headgear of any of embodiments 1-19 wherein the curved, switchable shutter comprises: a first polarizer having a first polarization direction; a second polarizer having a second polarization direction, which may be the same or different from the first polarization direction; and a first liquid-crystal cell disposed between the first and second polarizers, the liquid crystal cell containing first and second optically-transparent flexible layers that are curved and that have a first liquid crystal layer located between them. Embodiment 21 is the protective headgear of embodiment 20 wherein the curved, switchable shutter comprises a flexible front cover sheet that is an organic polymeric material and a flexible rear cover sheet that is an organic polymeric material. Embodiment 22 is the protective headgear of any of embodiments 1-3, 5-7, and 11-21 wherein the optical path includes exactly three antireflective layers: one on the major rear surface of the rear cover plate, one on the major front surface of the rear cover plate, and one on the major rear surface of the front cover plate.

EXAMPLE

A prototype curved cover plate was obtained by removing the transparent "lens" (transparent viewplate) from a product available from 3M Company, St. Paul Minn., under the trade designation FF-440 FULL FACEPIECE RESPIRATOR. The cover plate was cut to approximately 83 mm in height by 140 mm in length (along the lateral dimension of the cover plate). The cover plate, as obtained from the FF-440 product, was curved around a vertical axis and exhibited a radius of curvature that was estimated to be in the range of approximately 100 mm. The front-rear thickness of the cover plate was approximately 2 mm and was generally constant over the height of the cover plate and varied by approximately 10% over the lateral extent of the cover plate. The cover plate was comprised of clear polycarbonate and, as obtained from the FF-440 product, comprised a hardcoat on the front and rear major surfaces thereof.

The cover plate was placed into a vacuum chamber of an ebeam deposition apparatus. Four coatings, of alternating high and low index of refraction materials, were ebeam deposited to form a four-sub-layer antireflective layer. The composition and thickness of the four sub-layers was: sub-layer 1—$TiO_2$ (RI estimated to be in the range of approximately 2.3) at approximately 20 nm physical thickness; sub-layer 2—$MgF_2$ (RI estimated to be in the range of approximately 1.38) at approximately 40 nm physical thickness; sub-layer 3—$TiO_2$ at approximately 28 nm physical thickness; sub-layer 4—$MgF_2$ at approximately 120 nm physical thickness. Both major surfaces of the curved cover plate were coated in this manner, to obtain a curved cover plate that comprised antireflective layers on both major surfaces thereof. On each side of the cover plate, sub-layer 1 was closest to the cover plate (i.e., sub-layer 1 was deposited on the hardcoat); sub-layer 4 was furthest from the cover plate.

A similar four-sub-layer stack was coated onto a first major surface of a piece of clear, flexible polyester (PET) film. An optically clear pressure-sensitive adhesive (obtained from 3M Company under the trade designation 8211) was then laminated to the opposing, second major surface of the polyester film. The result was a PET film carrier layer bearing an antireflective layer thereon, which carrier layer could then be laminated to an optical component of a curved switchable shutter as described below.

Curved liquid crystal cells were made in generally similar manner to that described in the Example of U.S. Patent Application Publication 2014/0013479 to Magnusson. Two such cells were made. The cells were assembled together with polarizing films in generally similar manner to that described in the '479 Example, except that two liquid crystal cells and three polarizing films were used. An assembly was thus produced of the general type depicted in FIG. 9 of the present application, except that LC cell 20 and polarizer 22 were omitted. The assembly included a front bandpass filter that used a flexible glass substrate (of thickness approximately 0.1 mm), which flexible glass substrate served as a flexible front cover sheet of the assembly; the assembly further included a flexible glass substrate (again of thickness approximately 0.1 mm) that served as a flexible rear cover sheet of the assembly. The assembly thus provided a curved, switchable shutter of the general type described in the present application. A piece of the polyester carrier film bearing an antireflective layer on a first side thereof was laminated, by way of the optically clear adhesive, to the major rear surface of the flexible rear cover sheet of the curved, switchable shutter. The shutter thus comprised an antireflective layer disposed on a major rear surface thereof.

A prototype protective headgear (a welding helmet) was produced by rapid prototyping methods. The headgear comprised a front-facing opening (window) with a size, shape and curvature that was configured to receive the above-described curved front and rear cover plates and to receive the curved, switchable shutter. The cover plates and shutter were mounted in the window of the headgear, with the shutter being sandwiched between the two cover plates with front and rear air gaps therebetween. The switchable shutter (e.g. the liquid-crystal cells thereof) was electrically connected to a control apparatus and voltage source. A working, prototype protective headgear comprising an autodarkening filter was thus produced, the optical path of the headgear including a first antireflective layer on the major rear surface of the rear cover plate, a second antireflective layer on the major front surface of the rear cover plate, and a third antireflective layer on the major rear surface of the curved, switchable shutter.

In testing using human volunteers, the above-described Representative Example protective headgear was donned and was evaluated. While no quantitative data was obtained, volunteers reported qualitative observations that the optical performance (in terms of e.g. minimum ghosting, double images, and like phenomena) was noticeably enhanced in comparison to similar headgear that did not include antireflective layers. Variations on the above Representative Example were performed. In qualitative evaluation it appeared that, for example, providing an antireflective layer on at least one of the major surfaces of a curved front cover plate could result in at least a slight enhancement of the optical performance.

It will be apparent to those skilled in the art that the specific exemplary elements, structures, features, details, configurations, etc., that are disclosed herein can be modified and/or combined in numerous embodiments. All such variations and combinations are contemplated by the inventor as being within the bounds of the conceived invention, not merely those representative designs that were chosen to serve as exemplary illustrations. Thus, the scope of the present invention should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired. Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof). Although various theories and possible mechanisms may have been discussed herein, in no event should such discussions serve to limit the claimable subject matter. To the extent that there is any conflict or discrepancy between this specification as written and the disclosure in any document that is incorporated by reference herein, this specification as written will control.

What is claimed is:

1. A protective headgear comprising:
    an automatic darkening filter that comprises a curved switchable shutter that exhibits a curvature;
    a front cover plate that exhibits a curvature and that is positioned in front of the shutter; and,
    a rear cover plate that exhibits a curvature and that is positioned in rear of the shutter,
        wherein the front and rear cover plates and the shutter define an optical path that electromagnetic radiation can follow to reach the eyes of a wearer of the protective headgear;
        wherein the optical path includes a front air gap of from 0.5 mm to 4 mm between a major rear surface of the front cover plate and a major front surface of the curved switchable shutter, and further includes a rear air gap of from 0.5 mm to 4 mm between a major rear surface of the curved switchable shutter and a major front surface of the rear cover plate, and, wherein a total of two or three two antireflective layers are disposed on the optical path, including:

an antireflective layer disposed on the major rear surface of the curved switchable shutter; and, an antireflective layer disposed on the major front surface of the rear cover plate and/or an antireflective layer disposed on a major rear surface of the rear cover plate, and wherein no antireflective layer is present on the major front surface of the curved switchable shutter or on a major front surface or the major rear surface of the front cover plate.

2. The protective headgear of claim 1 wherein a total of two antireflective layers are disposed on the optical path.

3. The protective headgear of claim 2 wherein the two antireflective layers include an antireflective layer that is disposed on the major front surface of the rear cover plate.

4. The protective headgear of claim 2 wherein the two antireflective layers include an antireflective layer that is disposed on the major rear surface of the rear cover plate.

5. The protective headgear of claim 1 wherein a total of three antireflective layers are disposed on the optical path and wherein the three antireflective layers include an antireflective layer that is on the major front surface of the rear cover plate and an antireflective layer that is on the major rear surface of the rear cover plate.

6. The protective headgear of claim 1 wherein at least one of the antireflective layers is a single layer of material that exhibits a refractive index less than about 1.50.

7. The protective headgear of claim 1 wherein at least one of the antireflective layers is a multi-sublayer stack comprising two or three sublayers of materials that differ from each other in refractive index by at least about 0.3 and by at most 1.0.

8. The protective headgear of claim 1 wherein at least one of the antireflective layers is a multi-sublayer stack comprising four sublayers of materials that differ from each other in refractive index by at least about 0.3 and by at most 1.0.

9. The protective headgear of claim 8 wherein an outwardmost sublayer of the four sublayers exhibits a refractive index of at most about 1.5 and exhibits an optical thickness that is from about 80% to about 120% of a combined optical thickness of the other three sublayers.

10. The protective headgear of claim 1 wherein at least one of the antireflective layers is disposed on a carrier layer that is adhered to the major front surface or the major rear surface of the rear cover plate, by an optically clear adhesive.

11. The protective headgear of claim 1 wherein the curvature of the front cover plate is at least generally congruent with the curvature of the curved switchable shutter, and wherein the curvature of the rear cover plate is at least generally congruent with the curvature of the curved switchable shutter.

12. The protective headgear of claim 1 wherein the rear air gap of the optical path is between about 0.5 mm and about 2 mm and is at least substantially constant over a lateral extent of the rear air gap of the optical path.

13. The protective headgear of claim 1 wherein the front air gap between the major rear surface of the front cover plate and the major front surface of the curved switchable shutter is larger than the rear air gap between the major rear surface of the curved switchable shutter and the major front surface of the rear cover plate.

14. The protective headgear of claim 1 wherein the front cover plate and the rear cover plate are removable from the headgear.

15. The protective headgear of claim 1 wherein the curved, switchable shutter comprises:

a first polarizer having a first polarization direction;

a second polarizer having a second polarization direction, which may be the same or different from the first polarization direction; and a first liquid-crystal cell disposed between the first and second polarizers, the liquid crystal cell containing first and second optically-transparent flexible layers that are curved and that have a first liquid crystal layer located between them.

16. The protective headgear of claim 15 wherein the curved, switchable shutter comprises a flexible front cover sheet that is an organic polymeric material and a flexible rear cover sheet that is an organic polymeric material.

17. The protective headgear of claim 1 wherein the protective headgear is a welding helmet.

\* \* \* \* \*